United States Patent [19]
Sauer

[11] 3,986,212
[45] Oct. 19, 1976

[54] COMPOSITE PROSTHETIC DEVICE WITH POROUS POLYMERIC COATING

[75] Inventor: Barry W. Sauer, Central, S.C.

[73] Assignee: Glasrock Products, Inc., Atlanta, Ga.

[22] Filed: Apr. 11, 1975

[21] Appl. No.: 567,296

[52] U.S. Cl. .................................. 3/1.91; 3/1.912; 128/92 C; 3/1
[51] Int. Cl.² ........................................ A61F 1/24
[58] Field of Search .......................... 3/1, 1.9–1.913; 128/92 C, 92 CA, 334 R, 334 C; 32/10 A

[56] References Cited
UNITED STATES PATENTS

| | | | |
|---|---|---|---|
| 3,744,061 | 7/1973 | Frost | 3/1.912 |
| 3,765,033 | 10/1973 | Goldberg et al. | 3/1.911 |
| 3,790,507 | 2/1974 | Hodosh | 3/1.9 |
| 3,808,606 | 5/1974 | Tronzo | 3/1 |

OTHER PUBLICATIONS

"Porous Implant Systems for Prosthesis Stabilization", by C. A. Homsy et al., Reprint from Clinical Orthopaedics, No. 89, Nov.–Dec., 1972, pp. 220–235.
"The Role of Porous Polymeric Materials in Prosthesis Attachment", by B. W. Sauer et al., presented at the Clemson University Fifth Annual Biomaterial Symposium, Apr. 14–18, 1973, (8 pages).
"The Response of the Body Environment to Implants", by P. F. Williams, (chapter 5), *Implants in Surgery* by Williams & Roaf, W. B. Saunders Co. Ltd. publisher (London), July 3, 1973, p. 227.

*Primary Examiner*—Ronald L. Frinks
*Attorney, Agent, or Firm*—Lane, Aitken, Dunner & Ziems

[57] ABSTRACT

The invention is an improvement in a prosthetic device of the type that is a composite of a first material adapted to be strong enough to withstand the wear and stress exerted on the prosthetic device and a second material in the form of a coating fixed to the first material over a substantial portion of the outer surface of the prosthetic device that engages the bone to which the prosthetic device is attached. The coating is adapted to allow adjacent human tissue to grow therein. The improvement comprises the coating being at least 1 mm. thick and formed of a porous polymeric material that includes a network of interconnected pores throughout its volume. The average pore diameter of the coating ranges from 50 $\mu$m – 300 $\mu$m, the minimum pore volume being 30%.

9 Claims, 5 Drawing Figures

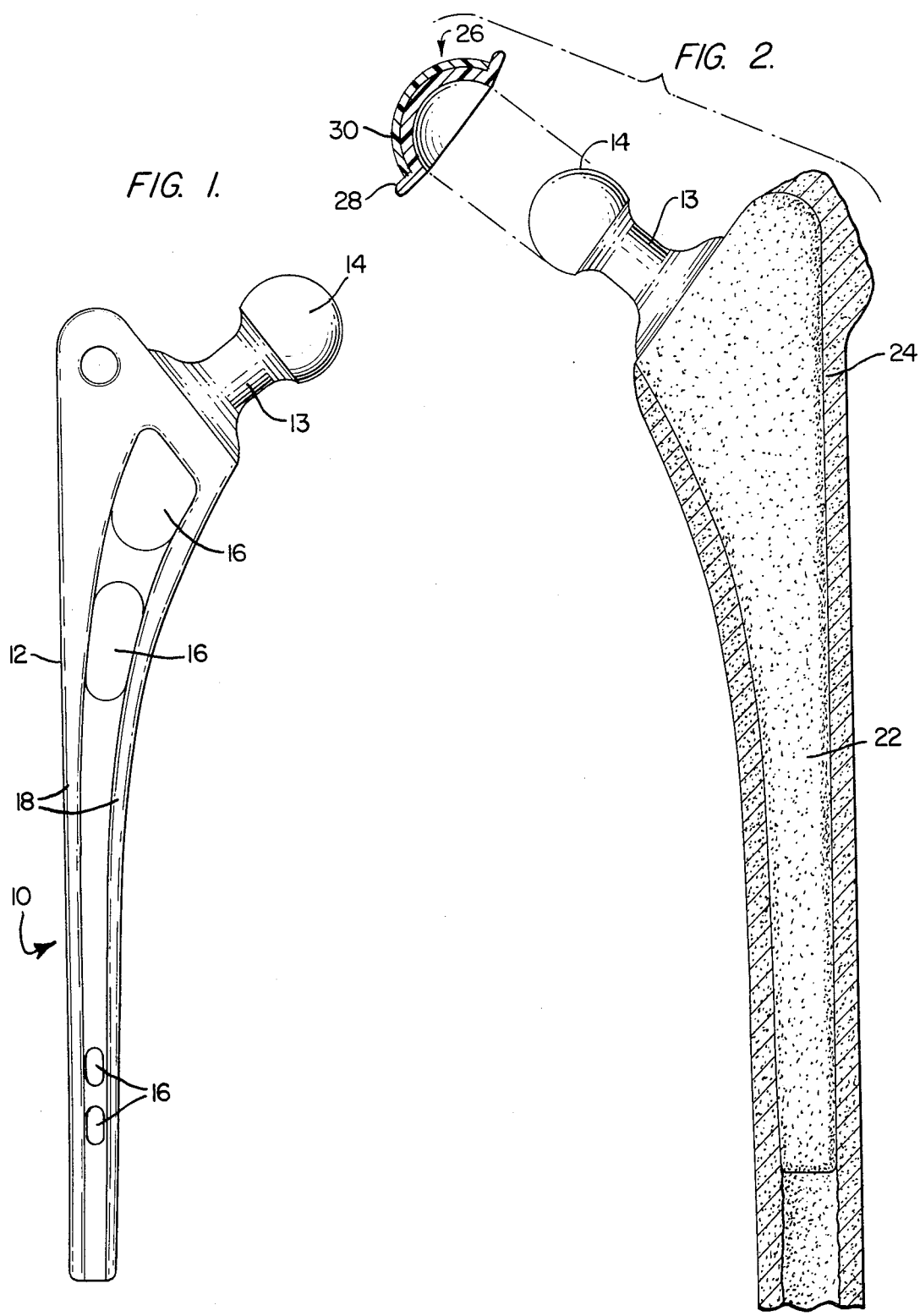

COMPOSITE PROSTHETIC DEVICE WITH POROUS POLYMERIC COATING

BACKGROUND OF THE INVENTION

This invention relates to prosthetic devices and more particularly to such prostheses that are formed as a composite that includes a layer or coating of porous polymeric material.

Most prostheses are fixed to the skeletal system by impacting a stem in the medullary canal of an appropriate bone or by mechanically fixing the device with a "bone cement" such as polymethylmethacrylate. However, these methods are not completely satisfactory because the devices tend to loosen upon impact or by use over a long period of time.

A phenomenon known as tissue ingrowth has been used in attempts to anchor prosthetic devices in place. Tissue ingrowth is where human tissue such as bone, tendons, blood vessels, etc., continues to grow after a prosthetic device is in place and will actually grow into and fill openings adjacent to the tissue. It has been recognized that ingrowth can be used to anchor prosthetic devices in place.

Polymeric materials such as polyethylene and polypropylene have been found to be suitable for use in prosthetic devices because of their biocompatibility and strength. Porous matrices of polyolefins and other polymers have been developed recently. These porous materials were evaluated successfully as a means of anchoring prosthetic devices.

A porous form of polyethylene and polypropylene has been developed. It has been suggested that this material be used for prosthesis attachment. However, since physical properties of porous materials tend to vary considerably with pore size and internal pore geometry, it was not know to what extent and how those materials could be used in prosthetic devices or what the essential physical characteristics of the material are for any such use.

SUMMARY OF THE INVENTION

In accordance with the invention it has been found that porous high density polyethylene and polypropylene, or mixtures thereof, within certain critical parameters can be used advantageously, for example in joint prostheses, by providing a coating of such material over a core or adjacent portion of a stronger material. The porous coating is applied to the portion of the prosthesis that is inserted into or otherwise engages the bone.

Such a coating can be mechanically interlocked to the stronger material or when a suitable stronger material is used the two can be chemically bonded together so that they are fixed relative to each other. After the prosthesis is implanted, surrounding tissue will grow into the pores until the device is firmly anchored in place.

It has been found that the feature of the porous high density polymeric materials which makes them particularly suited for use in prosthetic devices is that they include an internal network of interconnected pores without sacrificing any of the required strength. Furthermore, these pores are characterized by the fact that in the network there are, for the most part, no straight paths longer than the diameter of the largest pore, a feature which is defined by the term "tortuosity." This is advantageous because the ingrown tissue will more firmly anchor the prosthesis in place, as compared to other materials where the straight paths tend to be much longer. Tortuosity is considered to be important to provide an interlock between the prosthesis and the ingrown tissue that will prevent the prosthesis from becoming loose.

In order for the porous polymeric material to include a network of the proper pore size to allow the necessary tissue ingrowth and still retain the strength required to withstand stress to which such prosthesis are subjected, it has been found that the material must also have the following characteristics:

1. density — between 0.945 and 0.965 g./cc. for porous HDPE and between 0.912 and 0.914 g./cc. for porous polypropylene,
2. molecular weight number — greater than 450,000 and up to over 6,000,000 depending on the availability of such material, which is the relative mass of a compound calculated in the basis of an atomic weight for oxygen of 16 and is derived by multiplying the atomic weight of each element of the compound by the number of atoms of that element in the compound and adding them all together,
3. melt index — between 0.005 and 5 (ASTM D1238-57T), which includes the combination of materials of different melt indexes within the above range, such as for example a blend of porous HDPE comprising 20% by weight of 0.960 density and 5 melt index and 80% of 0.960 density and 0.01 melt index,
4. average pore diameter — between 50 $\mu$m and 300 $\mu$m, as determined by the bubble technique (ASTME 128) or by the Aminco Micro/Macro Porosimeter distributed by the American Instrument Company, and varies according to the tissue, tendons and/or bone in which the prosthesis is to be used,
5. average pore volume — minimum of 30% by weight, as determined by comparing the weight of the porous material with the weight of the material if it were not porous, which allows for proper random fixation (ingrowth) of the surrounding tissue without causing the device to fall below the minimum intrinsic strength needed to function properly.

It should also be kept in mind that although prostheses are preferably formed of porous HDPE or porous polypropylene or any other polymeric material that includes (1) the interconnected network of pores, (2) biocompatibility, and (3) the necessary strength characteristics, can be used.

BRIEF DESCRIPTION OF THE DRAWINGS

For a better understanding of the invention, reference may be had to the following description of several exemplary embodiments, taken in conjunction with the accompanying drawings, in which:

FIG. 1 is a plan view of the ball and stem portion of a hip joint prosthesis without but adapted to receive the porous polymeric coating, FIG. 2 is a plan view of the entire hip joint prosthesis of FIG. 1 with the porous polymeric coating applied thereto, the ball and stem portion being shown inserted into a femur and the cup portion being shown in section.

DETAILED DESCRIPTION OF EXEMPLARY EMBODIMENTS

Figure 3:
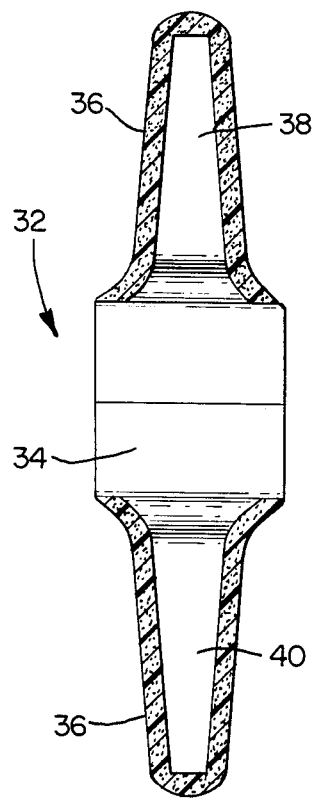
FIG. 3 is a top plan view, partially in section, of a finger joint prosthesis that includes the porous polymeric coating.

Several exemplary embodiments of inventive prosthetic devices will be described in detail in conjunction with the drawings. The two embodiments shown include a total hip joint prosthesis and a finger joint prosthesis. It should be kept in mind, however, that the invention can be applied to any joint in the body and to other areas where a high strength material is required and the claims herein should not be construed as restricted to the two specifically described embodiments.

Shown in FIG. 1 is the ball and stem portion of a hip joint prosthesis suitable for receiving a coating of porous polymeric material. The ball and stem portion, designated by the reference number 10, is adapted to be inserted in the medullary canal of the femur. This prosthetic device also includes a cup portion (not shown in FIG. 1) which is used to provide a new socket liner for the acetabulum. The portion 10 includes an elongated stem 12 which is driven into the medullary canal of the femur and engages the acetabulum. The stem 12 includes a plurality of openings 16 therein to provide a mechanical interlock with the porous polymeric coating. Alternatively other suitable surface geometrics, e.g. ridges, grooves or fenestrations, which provide a mechanical interlock with the porous coating could also be used. The stem 12 can also be formed with an I beam construction that includes the two ridge portions 18 along the outer ends thereof with a recessed portion therebetween.

The entire portion of the stem 12 that is inserted into the femur 20 is provided with the porous polymeric coating 22 which has the characteristics described in detail above, as shown best in FIG. 2 The core (which includes the stem 12, neck 13 and head 14) can be formed in one piece of any high strength biocompatible material. For the hip joint prosthesis it is preferable to use corrosion resistant metals such as chrome-cobalt alloys, stainless steel and titanium and its alloys. The coating 22 can be applied in any suitable way well known to those skilled in the art, such as for example by placing the stem portion in a mold and surrounding it by the porous polymeric material in powdered form and then heating the powder and removing the mold once the material has cured. It has been found that the coating should be at least about 1 mm. thick and preferably about 2–4 mm. thick to allow for sufficient tissue ingrowth.

As shown in FIG. 2, the coating completely covers the stem 12, leaving the neck 13 and head 14 exposed. The mechanical interlock provided by the holes 16 holds the coating firmly in place to prevent any shifting relative to the stem 12. The coated prosthetic device 10 is then inserted into the femur 20, as shown in FIG. 2, by removing the ball portion of the femur and exposing the medullary canal 24 into which the stem 12 is driven. The fact that the stem 12 extends into the medullary canal 24 will hold the prosthetic device 10 in place until the surrounding tissue has an opportunity to grow into the network of pores in the coating.

As is also shown in FIG. 2, the cup portion of the hip joint prosthesis, designated by reference number 26, includes the socket which engages the globular head 14. The socket is typically formed of ultra-high molecular weight polyethylene. The coating 30 of porous polymeric material discussed above is applied to the ultra-high molecular weight polyethylene by chemical bonding. In order to install the cup portion 26, the acetabulum is reamed out and the cup portion 26 is then implanted. The element 26 includes the peripheral flange 28 to provide extra support. Several small spikes (not shown) can be provided to project outwardly from the outer surface of the socket portion to hold it in place until the surrounding tissue has an opportunity to grow throughout the pores in the coating 30.

Figure 4:
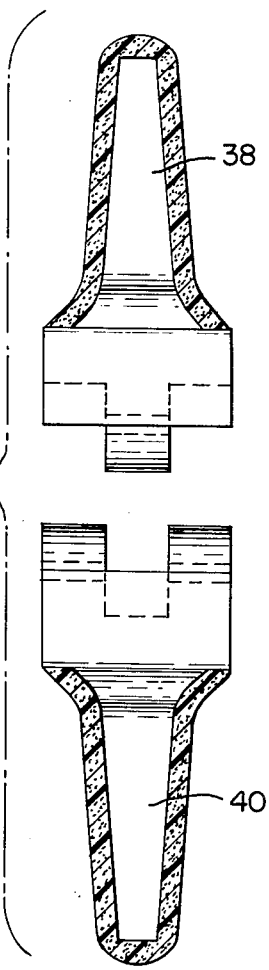
FIG. 4 is a bottom plan view, partially in section of the finger joint prosthesis shown in FIG. 3 that shows in particular the two elements disconnected.
Figure 5:
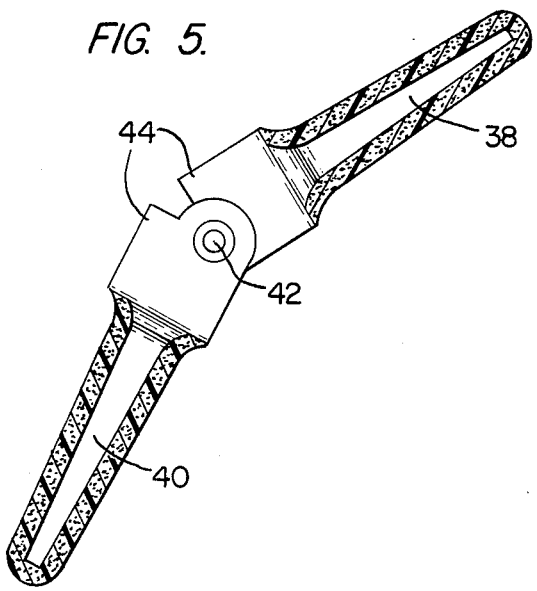
FIG. 5 is a side plan view, partially in section, of the finger joint prosthesis shown in FIGS. 3 and 4 that shows in particular the relative positions of the two elements when the finger is bent.

A second type of joint prosthesis that will be described in conjunction with the invention is that of a finger joint and is shown in FIGS. 3–5. The prosthetic device is indicated generally by reference numeral 32 and includes an inner core portion 34 that is preferably formed of solid ultra-high molecular weight polyethylene (molecular weight above 2 million). However, other suitable high strength materials could also be used. A coating of the porous polymeric material 36 is bonded to the core 34; in this case when the core 34 is formed of high density polyethylene the bond can be a chemical one. However, alternatively a mechanical bond such as the one shown for the hip joint prosthesis in FIGS. 1 and 2 can also be provided. Similarly to the hip joint prosthesis, the coating should be a minimum of about 1 mm. thick and preferably about 2–4 mm. thick.

The prosthesis 32 includes two sections 38, 40 which are connected as shown in FIGS. 4 and 5 by means of a hinge pin 42. The hinge pin 42 is preferably formed of a corrosion resistant metal such as the alloys mentioned above. The hinge axis should be slightly lower than the longitudinal axis of the prosthesis, as shown best in FIG. 5, and the stops 44 are provided so that the prosthesis can duplicate the bending capability of a normal finger joint.

The stem portion of each of the sections 38, 40 is inserted into the respective, intra-medullary canals of the adjacent finger bones to be connected by the joint. This is done by removing the head of the metacarpal and reaming the intra medullary canal of the metacarpal and the proximal phalanx to provide openings into which the prosthesis can be inserted.

As described above, the surrounding fiberous and bone tissue will grow into the porous material thereby anchoring the finger joint 32 in place.

Accordingly, a novel prosthetic device is provided which has an outer coating of porous polymeric material. This construction allows surrounding human tissue to grow into the interconnected pores such that the prosthesis will be anchored firmly in place without sacrificing adequate strength in the device. The embodiments of the invention described above are intended to be merely exemplary and those skilled in the art will be able to make modifications and variations thereto without departing from the spirit and scope of the appended claims.

I claim:

1. An improvement in a prosthetic device of the type that is a composite of a first material adopted to be strong enough to withstand the wear and stress exerted on the prosthetic device and a second material in the form of a coating fixed to the first material over a substantial portion of the outer surface of the prosthetic device that engages the tissue to which the prosthetic device is attached, the coating being adapted to allow adjacent human tissue to grow therein, the improvement comprising the coating being at least 1 mm. thick and formed of a porous polymeric material with a density of at least 0.912 g./cc. that includes a network of inter-connected pores throughout its volume with no straight paths therein longer than the diameter of the largest pore, the average pore diameter ranging from 50 µm – 300 µm, the minimum pore volume being 30%.

2. The improvement in claim 1, wherein the coating has a maximum thickness of 3 mm.

3. The improvement in claim 1, wherein the coating is mechanically fixed to the first material.

4. The improvement in claim 3, wherein the first material includes a plurality of openings therethrough and the coating substantially completely filling said openings.

5. The improvement in claim 1, wherein the coating is chemically bonded to said first material.

6. The improvement in claim 1, wherein the polymeric material comprises polyethylene having a density in the range of 0.945 to 0.965 g./cc.

7. The improvement in claim 1, wherein the polymeric material comprises polypropylene having a density in the range of 0.912 to 0.914 g./cc.

8. The improvement in claim 1, wherein the prosthetic device includes two cooperating elongated portions, each of which is adapted to be inserted into the medullary canal of one of a pair of bones that form a joint therebetween hinge means for connecting the two portions, each of said two portions being formed as a composite of said first material and said coating.

9. The improvement in claim 1, wherein the prosthetic device includes a ball portion with an elongated portion adapted to be inserted into the medullary canal of a bone, said elongated portion being formed as a composite of said first material and said coating, the prosthetic device further including a socket portion adapted to receive said ball portion, said socket being formed as a composite of said first material and said coating with the first material part of said socket engaging said ball portion.

* * * * *